(12) United States Patent
Lang et al.

(10) Patent No.: US 6,797,013 B1
(45) Date of Patent: *Sep. 28, 2004

(54) OXIDATION DYEING COMPOSITION FOR KERATINOUS FIBRES CONTAINING A 3-AMINOPYRIDINE AZO DERIVATIVE AND DYEING METHOD USING SAID COMPOSITION

(75) Inventors: Gérard Lang, Saint Prix (FR); Jean Cotteret, Verneuil-sur-Seine (FR); Mireille Maubru, Chatou (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,119

(22) PCT Filed: Mar. 11, 1999

(86) PCT No.: PCT/FR99/00541

§ 371 (c)(1),
(2), (4) Date: Jan. 5, 2000

(87) PCT Pub. No.: WO99/48465

PCT Pub. Date: Sep. 30, 1999

(30) Foreign Application Priority Data

Mar. 20, 1998 (FR) .......................................... 98 03454

(51) Int. Cl.$^7$ ................................................ C09K 7/13
(52) U.S. Cl. ...................... 8/409; 8/407; 8/423; 8/426
(58) Field of Search ........................... 8/407, 409, 423, 8/426

(56) References Cited

U.S. PATENT DOCUMENTS

| 4,025,301 A | | 5/1977 | Lang ............................... 8/426 |
| 4,213,758 A | * | 7/1980 | Rose et al. ..................... 8/409 |
| 5,061,289 A | * | 10/1991 | Clausen et al. ................. 8/405 |

FOREIGN PATENT DOCUMENTS

| DE | 23 59 399 | 6/1975 |
| DE | 38 43 892 | 6/1990 |
| DE | 41 33 957 | 4/1993 |
| DE | 42 34 886 | 4/1994 |
| DE | 42 34 887 | 4/1994 |
| DE | 42 41 173 | 6/1994 |
| DE | 195 43 988 | 5/1997 |
| EP | 0 739 622 | 10/1996 |
| EP | 0 850 638 | 7/1998 |
| FR | 2 285 851 | 4/1976 |
| FR | 2 586 913 | 3/1987 |
| FR | 2 733 749 | 11/1996 |
| FR | 2 735 685 | 12/1996 |
| FR | 2 750 048 | 12/1997 |
| GB | 1 026 978 | 4/1966 |
| GB | 1 153 196 | 5/1969 |
| WO | WO 94/08969 | 4/1994 |
| WO | WO 94/08970 | 4/1994 |
| WO | WO 96/15765 | 5/1996 |
| WO | WO 97/39727 | 10/1997 |

OTHER PUBLICATIONS

English language abstract of EP 0 739 622, Oct. 1996.
English language abstract of EP 0 850 638, Jul. 1998.
English language Derwent Abstract of FR 2 285 851, Apr. 1976.
English language abstract of FR 2 586 913, Mar. 1987.
English language abstract of FR 2 735 685, Dec. 1996.
English language abstract of FR 2 733 749, Nov. 1996.
English language Derwent Abstract of FR 2 750 048, Dec. 1997.
English language Derwent Abstract of JP 2019576, Jan. 1990.
Dorothy Nickerson et al., "Color Tolerance Specification", Journal of the Optical Society of America, vol. 34, No. 9, Sep. 1944, pp. 550–570.
English language Derwent Abstract of DE 23 59 399, Jun. 1975.
English language abstract of DE 38 43 892, Jun. 1990.
English language abstract of DE 41 33 957, Apr. 1993.
English language abstract of DE 42 34 886, Apr. 1994.
English language abstract of DE 42 34 887, Apr. 1994.
English language abstract of DE 42 41 173, Jun. 1994.
English language Derwent Abstract of DE 195 43 988, May 1997.

* cited by examiner

Primary Examiner—Margaret Einsmann
(74) Attorney, Agent, or Firm—Finnegan, Henderson, Farabow, Garrett & Dunner, L.L.P.

(57) ABSTRACT

The invention relates to a composition for the oxidation dyeing of keratin fibres, and in particular human keratin fibres such as the hair, comprising, in a medium which is suitable for dyeing, at least one heterocyclic oxidation base and at least one 3-aminopyridine derivative as direct dye, as well as to the dyeing process using this composition.

23 Claims, No Drawings

OXIDATION DYEING COMPOSITION FOR KERATINOUS FIBRES CONTAINING A 3-AMINOPYRIDINE AZO DERIVATIVE AND DYEING METHOD USING SAID COMPOSITION

The invention relates to a composition for the oxidation dyeing of keratin fibres, and in particular human keratin fibres such as the hair, comprising, in a medium which is suitable for dyeing, at least one heterocyclic oxidation base and at least one 3-aminopyridine derivative as direct dye, as well as to the dyeing process using this composition.

It is known practice to dye keratin fibres, and in particular human hair, with dye compositions containing oxidation dye precursors, in particular ortho- or para-phenylenediamines, ortho- or para-aminophenols and heterocyclic bases, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used as regards the oxidation bases and couplers allows a wide range of colours to be obtained.

It is also known that, in order to vary the shades obtained even more and to give them glints, it is possible to use, in combination with the oxidation dye precursors and couplers, direct dyes, i.e. coloured substances which provide a coloration in the absence of an oxidizing agent.

The great majority of these direct dyes belong to the family of nitrobenzene compounds and have the drawback, when they are incorporated into dye compositions, of leading to colorations that are not sufficiently fast, in particular with respect to shampoos.

The so-called "permanent" coloration obtained by means of these oxidation dyes must moreover satisfy a certain number of requirements. Thus, it must be able to give shades of the desired intensity and it must be able to withstand external agents (light, bad weather, washing, permanent-waving, perspiration and rubbing).

The dyes must also make it possible to cover white hair, and, finally, they must be as unselective as possible, i.e. they must give the smallest possible differences in colour all the way along the same keratin fibre, which may indeed be differently sensitized (i.e. damaged) between its tip and its root.

Compositions for the oxidation dyeing of keratin fibres containing a combination of a benzenic oxidation base and a direct dye of the 3-aminopyridine family have already been proposed, in particular in patent application FR-A-2,285,851. However, the colorations obtained using such compositions are not entirely satisfactory, in particular from the point of view of their chromaticity and their fastness.

The Applicant has now discovered that it is possible to obtain novel dyes which are capable of giving intense and chromatic colorations, which show little selectivity and which satisfactorily withstand the various attacking factors to which the fibres may be subjected, by combining at least one heterocyclic oxidation base and at least one suitably selected 3-aminopyridine derivative as direct dye.

This discovery forms the basis of the present invention.

A first subject of the invention is thus a composition for the oxidation dyeing of keratin fibres, and in particular of human keratin fibres such as the hair, characterized in that it comprises, in a medium which is suitable for dyeing:

at least one heterocyclic oxidation base and as direct dye, at least one 3-aminopyridine derivative chosen from the compounds of formula (I) below:

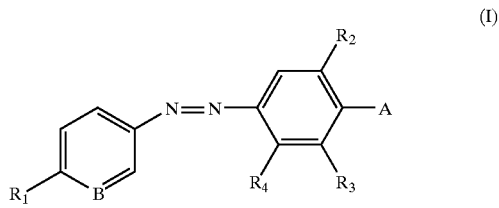

in which:

B represents a group of formula (Ia) or (Ib) below:

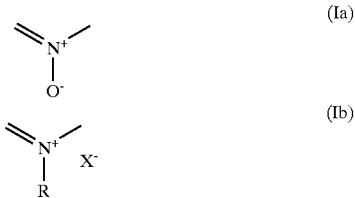

R represents a $C_1$–$C_4$ alkyl radical;

$R_1$ represents a hydrogen or halogen atom such as chlorine, bromine or fluorine, or a $C_1$–$C_4$ alkyl or $C_1$–$C_4$ alkoxy radical;

$R_2$ represents a hydrogen atom or a $C_1$–$C_4$ alkyl or $C_1$–$C_4$ alkoxy radical;

$R_4$ represents a hydrogen or halogen atom such as chlorine, bromine or fluorine, or a $C_1$–$C_4$ alkyl, nitro, amino or ($C_1$–$C_4$)acylamino radical;

$R_3$ represents a hydrogen atom or else $R_4$ and $R_3$ together form a 6-membered unsaturated ring bearing a hydroxyl substituent chelated with one of the nitrogen atoms of the azo double bond;

A represents a residue —$NR_5R_6$ in which $R_5$ represents a hydrogen atom or a $C_1$–$C_4$ alkyl, $C_1$–$C_4$ monohydroxyalkyl or $C_2$–$C_4$ polyhydroxyalkyl radical; $R_6$ represents a hydrogen atom, a $C_1$–$C_4$ alkyl, $C_1$–$C_4$ monohydroxyalkyl or $C_2$–$C_4$ polyhydroxyalkyl radical, a phenyl ring or a —$CH_2$—$SO_3Na$ radical;

$X^-$ represents a monovalent or divalent anion and is preferably chosen from a halogen atom such as chlorine, bromine, fluorine or iodine, a hydroxide, a hydrogen sulphate or a ($C_1$–$C_6$)alkyl sulphate such as, for example, a methyl sulphate or an ethyl sulphate.

The dye composition in accordance with the invention gives intense, chromatic colorations which show little selectivity and excellent properties of resistance both with respect to atmospheric agents such as light and bad weather, and with respect to perspiration and the various treatments to which the hair may be subjected. These properties are particularly noteworthy as regards the chromaticity.

A subject of the invention is also a process for the oxidation dyeing of keratin fibres using this dye composition.

The heterocyclic oxidation base(s) is(are) preferably chosen from pyridine derivatives, pyrimidine derivatives and pyrazole derivatives, and the addition salts thereof with an acid.

Among the pyridine derivatives, mention may be made more particularly of the compounds described, for example, in GB patents 1,026,978 and 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-333,495, such as 2,4,5,6-tetraaminopyrimidine, 4-hydroxy-2,5,6-triaminopyrimidine, and the addition salts thereof with an acid, and also pyrazolopyrimidine derivatives, such as pyrazolo[1,5-a]pyrimidine-3,7-diamine, 2-methyl-pyrazolo[1,5-a]pyrimidine-3,7-diamine, 2,5-dimethyl-pyrazolo[1,5-a]pyrimidine-3,7-diamine, pyrazolo-[1,5-a]pyrimidine-3,5-diamine, 2,7-dimethylpyrazolo-[1,5-a]pyrimidine-3,5-diamine, 3-aminopyrazolo[1,5-a]-pyrimidin-7-ol, 3-amino-5-methylpyrazolo[1,5-a]-pyrimidin-7-ol, 3-aminopyrazolo[1,5-a]pyrimidin-5-ol, 2-(3-aminopyrazolo[1,5-a]pyrimidin-7-ylamino)ethanol, 3-amino-7-β-hydroxyethylamino-5-methylpyrazolo[1,5-a]-pyrimidine, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-amino-pyrazolo[1,5-a]pyrimidin-3-yl)-(2-hydroxyethyl)-amino]ethanol, 5,6-dimethylpyrazolo[1,5-a]pyrimidine-3,7-diamine, 2,6-dimethylpyrazolo[1,5-a]pyrimidine-3,7-diamine and 2,5, N7,N7-tetramethylpyrazolo[1,5-a]-pyrimidine-3,7-diamine, and the addition salts thereof and the tautomeric forms thereof, when a tautomeric equilibrium exists.

Among the pyrazole derivatives, mention may be made more particularly of the compounds described in patents or patent applications DE 3,843,892, DE 4,133,957, DE 4,234,886, DE 4,234, 887, FR 2,733,749, FR 2,735,685, WO 94/08969 and WO 94/08970, such as 4,5-diaminopyrazole, 4,5-diamino-1-methylpyrazole, 1-benzyl-4,5-diaminopyrazole, 3,4-diaminopyrazole, 1-benzyl-4,5-diamino-3-methylpyrazole, 4-amino-1,3-dimethyl-5-hydrazinopyrazole, 4,5-diamino-3-methyl-1-phenyl-pyrazole, 4,5-diamino-3-methyl-1-tert-butylpyrazole, 4,5-diamino-1-methyl-3-tert-butylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, and the addition salts thereof with an acid.

The heterocyclic oxidation base(s) preferably represent(s) from 0.0005 to 12% by weight approximately relative to the total weight of the dye composition in accordance with the invention, and even more preferably from 0.005 to 6% by weight approximately relative to this weight.

The 3-aminopyridine derivative(s) of formula (I) in accordance with the invention is (are) preferably chosen from:

4'-dimethylaminobenzene-1'-azo-1-methyl-3-pyridinium methosulphate of formula:

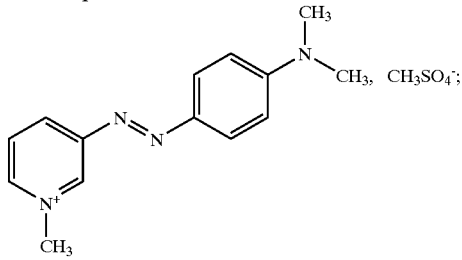

4'-bis(β-hydroxyethyl)aminobenzene-1'-azo-1-methyl-3-pyridinium methosulphate of formula:

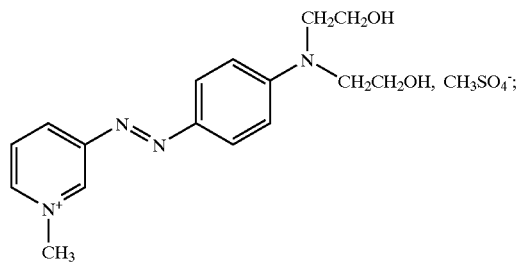

4'-amino-8'-hydroxynaphthalene-1'-azo-1-methyl-3-pyridinium methosulphate of formula:

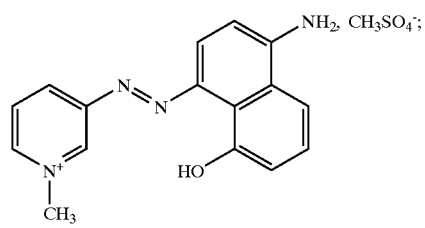

4'-dimethylamino-2'-nitrobenzene-1'-azo-1-methyl-3-pyridinium methosulphate of formula:

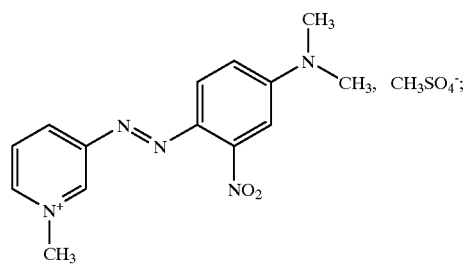

4'-dimethylaminobenzene-1'-azo-1,6-dimethyl-3-pyridinium methosulphate of formula:

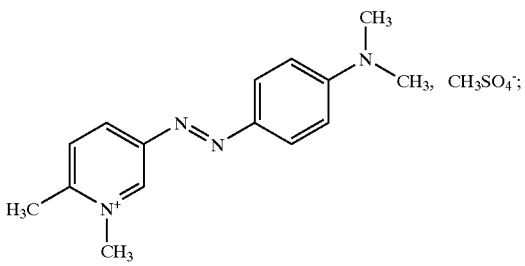

4'-aminobenzene-1'-azo-3-pyridine N-oxide of formula:

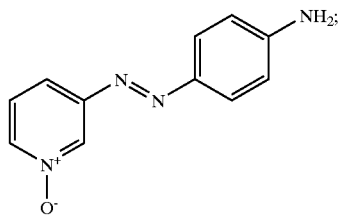

4'-dimethylaminobenzene-1'-azo-3-pyridine N-oxide of formula:

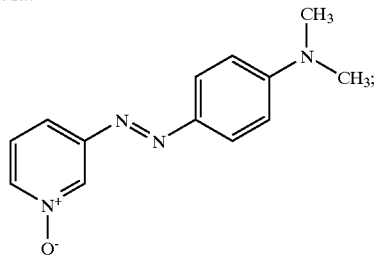

4'-N,N-bis(β-hydroxyethyl)aminobenzene-1'-azo-3-pyridine N-oxide of formula:

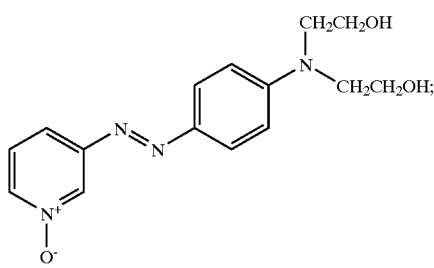

4'-dimethylamino-2'-methylbenzene-1'-azo-1-ethyl-3-pyridinium ethosulphate of formula:

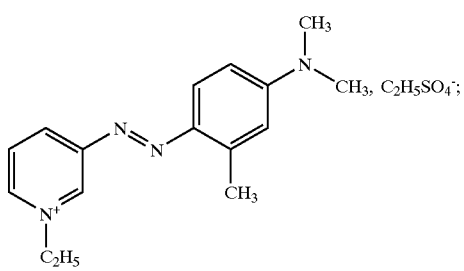

4'-dimethylamino-2'-methylbenzene-1'-azo-1-butyl-3-pyridinium bromide of formula:

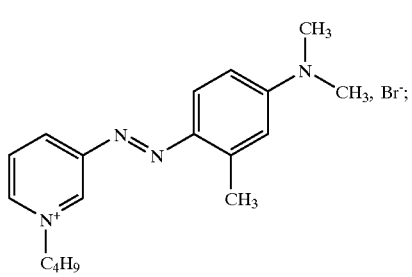

4'-dimethylamino-2'-chlorobenzene-1'-azo-1-methyl-3-pyridinium methosulphate of formula:

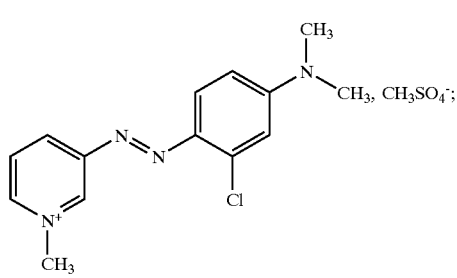

2',4'-diamino-5'-methylbenzene-1'-azo-1-methyl-3-pyridinium methosulphate of formula:

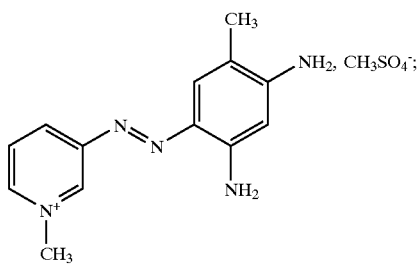

4'-phenylaminobenzene-1'-azo-1-methyl-3-pyridinium methosulphate of formula:

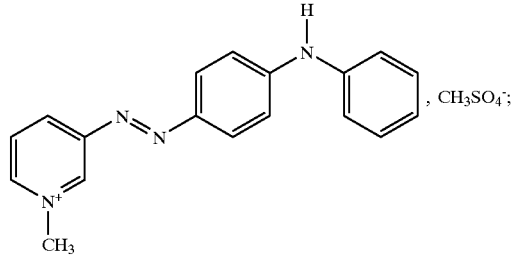

2'-acetylamino-4'-dimethylaminobenzene-1'-azo-1-ethyl-3-pyridinium ethosulphate of formula:

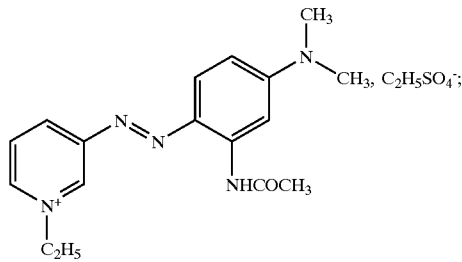

2',4'-diamino-5'-methoxybenzene-1'-azo-1-methyl-3-pyridinium methosulphate of formula:

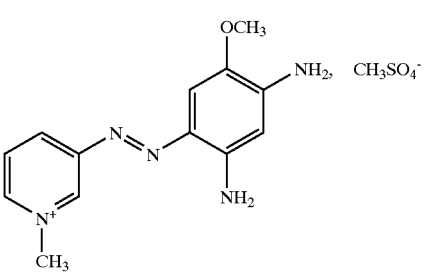

and
2'-amino-4'-dimethylaminobenzene-1'-azo-1-methyl-3-pyridinium methosulphate of formula:

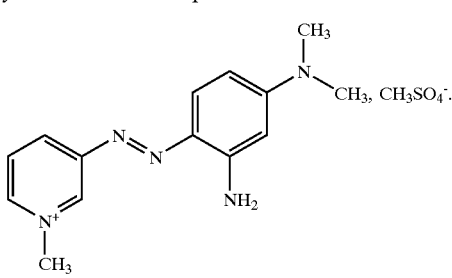

The 3-aminopyridine derivative(s) of formula (I) used according to the invention preferably represent(s) from 0.001 to 10% by weight approximately relative to the total weight of the dye composition, and even more preferably from 0.01 to 5% by weight approximately relative to this weight.

The dye composition in accordance with the invention can also contain one or more couplers and/or one or more benzenic oxidation bases and/or one or more direct dyes other than the 3-aminopyridine derivatives of formula (I), in particular to modify the shades or to enrich them with glints.

Among the couplers which may be present in the dye composition in accordance with the invention, mention may be made in particular of meta-phenylenediamines, meta-aminophenols, meta-diphenols and heterocyclic couplers, and the addition salts thereof with an acid.

When they are present, these additional couplers preferably represent from 0.0001 to 10% by weight approximately relative to the total weight of the dye composition and even more preferably from 0.005 to 5% by weight approximately relative to this weight.

Among the benzenic oxidation bases which may be additionally present in the dye composition in accordance with the invention, mention may be made in particular of para-phenylenediamines, para-aminophenols, ortho-aminophenols and double bases such as bis(phenyl) alkylenediamines.

When they are present, these benzenic bases preferably represent from 0.0005 to 12% by weight approximately relative to the total weight of the dye composition in accordance with the invention, and even more preferably from 0.005 to 6% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) for the dye composition in accordance with the invention generally consists of water or of a mixture of water and at least one organic solvent to dissolve the compounds which would not be sufficiently soluble in water. Organic solvents which may be mentioned, for example, are $C_1$–$C_4$ alkanols, such as ethanol and isopropanol.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 12 approximately. It can be adjusted to the desired value by means of acidifying or basifying agents usually used for dyeing keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid or lactic acid, and sulphonic acids.

Among the basifying agents which may be mentioned, for example, are aqueous ammonia, alkaline carbonates, alkanolamines such as mono-, di- and triethanolamine, 2-methyl-2-aminopropanol and derivatives thereof, sodium hydroxide, potassium hydroxide and the compounds of formula (II) below:

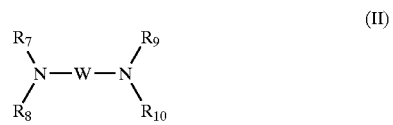

in which W is a propylene residue optionally substituted with a hydroxyl group or a $C_1$–$C_4$ alkyl radical; $R_7$, $R_8$, $R_9$ and $R_{10}$, which may be identical or different, represent a hydrogen atom or a $C_1$–$C_4$ alkyl or $C_1$–$C_4$ hydroxyalkyl radical.

The dye composition in accordance with the invention can also contain various adjuvants conventionally used in compositions for dyeing the hair.

Needless to say, a person skilled in the art will take care to select this or these optional additional compounds such that the advantageous properties intrinsically associated with the dye composition in accordance with the invention are not, or are not substantially, adversely affected by the addition or additions envisaged.

The dye composition in accordance with the invention can be in various forms, such as in the form of liquids, creams or gels, which are optionally pressurized, or in any other form which is suitable for dyeing keratin fibres, and in particular human hair.

A subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH with the aid of an oxidizing agent which is added to the dye composition only at the time of use, or which is present in an oxidizing composition that is applied simultaneously or sequentially in a separate manner.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left on them for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates, persalts such as perborates and persulphates, peracids, enzymes such as 2-electron oxidoreductases, peroxidases and lactases. Hydrogen peroxide is particularly preferred.

The pH of the oxidizing composition containing the oxidizing agent as defined above is such that, after mixing with the dye composition, the pH of the resulting composition applied to the keratin fibres preferably ranges between 3 and 12 approximately and even more preferably between 5 and 11. It is adjusted to the desired value by means of acidifying or basifying agents usually used for dyeing keratin fibres and are as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or in any other form which is suitable for dyeing keratin fibres, and in particular human hair.

Another subject of the invention is a multi-compartment dyeing device or multi-compartment dyeing "kit", or any other multi-compartment packaging system, a first compartment of which contains the dye composition as defined above and a second compartment of which contains the oxidizing composition as defined above. These devices may be equipped with a means for applying the desired mixture to the hair, such as the devices described in patent FR-2,586,913 in the name of the Applicant.

The examples which follow are intended to illustrate the invention without thereby limiting its scope.

EXAMPLES

Comparative Dyeing Examples 1 to 4

The dye compositions below were prepared (contents in grams):

| EXAMPLE | 1 | 2(*) | 3 | 4(*) |
|---|---|---|---|---|
| 4'-Dimethylaminobenzene-1'-azo-3-pyridine N-oxide (compound of formula (I)) | 0.5 | 0.5 | — | — |
| 2'-Acetylamino-4'-dimethyl-aminobenzene-1'-azo-1-ethyl-3-pyridinium ethosulphate (compound of formula (I)) | — | — | 0.6 | 0.6 |
| 4,5-Diamino-1-ethyl-3-methylpyrazole dihydrochloride (heterocyclic oxidation base) | 0.639 | — | 0.639 | — |
| para-Phenylenediamine (oxidation base) | — | 0.324 | — | 0.324 |
| meta-Aninophenol (coupler) | 0.327 | 0.327 | 0.327 | 0.327 |
| Common dye support | () | () | () | () |
| Demineralized water qs | 100 g | 100 g | 100 g | 100 g |

(*)Comparative example not forming part of the invention
(**) Common dye support:

| | |
|---|---|
| -Oleyl alcohol polyglycerolated with 2 mol of glycerol | 4.0 g |
| -Oleyl alcohol polyglycerolated with 4 mol of glycerol, containing 78% active material (A.M.) | 5.69 g A.M. |
| -Oleic acid | 3.0 g |
| -Oleylamine containing 2 mol of ethylene oxide, sold under the trade name Ethomeen O12 ® by the company Akzo | 7.0 g |
| -Diethylaminopropyl laurylaminosuccinamate, sodium salt, containing 55% A.M. | 3.0 g A.M. |
| -Oleyl alcohol | 5.0 g |
| -Oleic acid diethanolamide | 12.0 g |
| -Propylene glycol | 3.5 g |
| -Ethyl alcohol | 7.0 g |
| -Dipropylene glycol | 0.5 g |
| -Propylene glycol monomethyl ether | 9.0 g |
| -Sodium metabisulphite as an aqueous solution containing 35% A.M. | 0.455 g A.M. |
| -Ammonium acetate | 0.8 g |
| -Antioxidant, sequestering agent | qs |
| -Fragrance, preserving agent | qs |
| -Aqueous ammonia containing 20% $NH_3$ | 10.0 g |

Each of the dye compositions described above was mixed, at the time of use, with an equivalent weight-amount of 20-volumes hydrogen peroxide (6% by weight) having a pH of about 3.

Each resulting mixture had a pH of about 10±0.2 and was applied for 30 minutes to locks of permanent-waved grey hair containing 90% white hairs.

The hair was then rinsed with water, washed with a standard shampoo, rinsed again and then dried.

The colour of the locks was evaluated before and after dyeing, in the Munsell system, using a Minolta CM 2002® spectrophotometer.

According to the Munsell notation, a colour is defined by the formula: in which the three parameters denote, respectively, the "Hue" or shade (H), the "Value" or intensity (V) and the "Chroma" or saturation (C), the oblique line simply being a convention and not denoting a ratio.

The increase in the coloration ΔE can be calculated by applying the Nickerson equation:

$$\Delta E = 0.4 C_0 dH + 6 dV + 3 dC$$

as described, for example, in "Journal of the Optical Society of America", vol. 34, No. 9, Sept 1944, pages 550–570.

In this equation, ΔE represents the difference in colour between two locks (in the present case the increase in the coloration), dH, dv and dC represent the variation in absolute value of the three parameters H, V and C, $C_0$ representing the saturation of the lock relative to which it is desired to evaluate the difference in colour.

The greater the value of ΔE,thearch greater the difference in colour between the two locks, and, in the present case, the greater the increase (intensity) in the coloration.

The results are given in the table below:

| Example | Colour of the lock before dyeing | Colour of the lock after dyeing | Increase in coloration | | | |
|---|---|---|---|---|---|---|
| | | | dH | dV | dC | ΔE |
| 1 | 3.3 Y 5.8/1.6 | 7.5 R 2.7/3.5 | 15.8 | 3.1 | 1.9 | 34.4 |
| 2(*) | 3.3 Y 5.8/1.6 | 1.2 YR 2.4/2.1 | 12.1 | 3.4 | 0.5 | 29.6 |
| 3 | 3.3 Y 5.8/1.6 | 1.5 R 2.6/3.3 | 21.8 | 3.2 | 1.7 | 38.3 |
| 4(*) | 3.3 Y 5.8/1.6 | 8.7 R 2.2/1.5 | 14.6 | 3.6 | 0.1 | 31.2 |

(*)Comparative example not forming part of the invention

It is found that the dye compositions of Examples 1 and 3 in accordance with the invention, i.e. compositions containing a combination of a direct dye of formula (I), a heterocyclic oxidation base and a coupler, lead to more intense colorations than the dye compositions of Examples 2 and 4 not forming part of the invention since they contain a benzenic oxidation base instead of the heterocyclic oxidation base and as described, for example, in patent application FR-A-2,285,851.

What is claimed is:

1. A composition for the oxidation dyeing of keratin fibers, comprising:
   a) at least one heterocyclic oxidation base chosen from pyridine derivatives and pyrimidine derivatives, and acid addition salts thereof, and
   b) as a direct dye, at least one 3-aminopyridine derivative chosen from the compounds of formula (I):

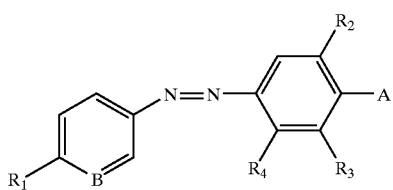

in which:

B is chosen from formula (Ia) or (Ib):

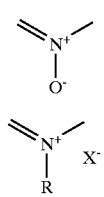

R is a $C_1$–$C_4$ alkyl radical;

$R_1$ is chosen from a hydrogen atom, a halogen atom, a $C_1$–$C_4$ alkyl radical, and a $C_1$–$C_4$ alkoxy radical;

$R_2$ is chosen from a hydrogen atom, a $C_1$–$C_4$ alkyl radical and a $C_1$–$C_4$ alkoxy radical;

$R_4$ is chosen from a hydrogen atom, a halogen atom, a $C_1$–$C_4$ alkyl radical, a nitro radical, an amino radical and a ($C_1$–$C_4$)acylamino radical;

$R_3$ is a hydrogen atom, or $R_4$ and $R_3$ together form a 6-membered unsaturated ring bearing a hydroxyl substituent chelated with one of the nitrogen atoms of the azo double bond;

A is a residue —$NR_5R_6$ in which $R_5$ is chosen from a hydrogen atom, a $C_1$–$C_4$ alkyl radical, a $C_1$–$C_4$ monohydroxyalkyl radical and a $C_2$–$C_4$ polyhydroxyalkyl radical; and $R_6$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a phenyl ring and a —$CH_2$—$SO_3Na$ radical; and $X^-$ is chosen from a monovalent anion and a divalent anion.

2. A composition according to claim 1, wherein said keratin fibers are human keratin fibers.

3. A composition according to claim 2, wherein said human keratin fibers are human hair.

4. A composition according to claim 1, wherein said composition is in a medium suitable for dyeing.

5. A composition according to claim 1, wherein said halogen atom is chosen from chlorine, bromine and fluorine.

6. A composition according to claim 1, wherein said $X^-$ is chosen from a halogen atom, a hydroxide, a hydrogen sulfate and a ($C_1$–$C_6$)alkyl sulfate.

7. A composition according to claim 6, wherein said halogen atom is chosen from chlorine, bromine, fluorine and iodine.

8. A composition according to claim 6, wherein said ($C_1$–$C_6$)alkyl sulfate is chosen from a methyl sulfate and an ethyl sulfate.

9. A composition according to claim 1, wherein said pyridine derivatives are chosen from 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

10. A composition according to claim 1, wherein said pyrimidine derivatives are chosen from 2,4,5,6-tetraaminopyrimidine, 4-hydroxy-2,5,6-triaminopyrimidine, pyrazolo[1,5-a]pyrimidine-3,7-diamine, 2-methylpyrazolo[1,5-a]pyrimidine-3,7-diamine, 2,5-dimethylpyrazolo[1,5-a]pyrimidine-3,7-diamine, pyrazolo-[1,5-a]pyrimidine-3,5-diamine, 2,7-dimethylpyrazolo-[1,5-a]pyrimidine-3,5-diamine, 3-aminopyrazolo[1,5-a]pyrimidin-7-ol, 3-amino-5-methylpyrazolo[1,5-a]pyrimidin-7-ol, 3-amino-pyrazolo[1,5-a]pyrimidin-5-ol, 2-(3-aminopyrazolo[1,5-a]pyrimidin-7-ylamino)ethanol, 3-amino-7-β-hydroxy-ethylamino-5-methylpyrazolo[1,5-a]pyrimidine, 2-(7-aminopyrazolo[1,5-a]pyrimidin-3-ylamino)ethanol, 2-[(3-aminopyrazolo[1,5-a]pyrimidin-7-yl)-(2-hydroxyethyl)-amino]ethanol, 2-[(7-aminopyrazolo[1,5-a]pyrimidin-3-yl)-(2-hydroxyethyl)amino]ethanol, 5,6-dimethyl-pyrazolo[1,5-a]pyrimidine-3,7-diamine, 2,6-dimethyl-pyrazolo[1,5-a]pyrimidine-3,7-diamine and 2,5 N7,N7-tetramethylpyrazolo[1,5-a]pyrimidine-3,7-diamine, the addition salts thereof and the tautomeric forms thereof, when a tautomeric equilibrium exists.

11. A composition according to claim 1, wherein said at least one heterocyclic oxidation base is present in an amount ranging from about 0.0005 to about 12% by weight relative to the total weight of the dye composition.

12. A composition according to claim 11, wherein said at least one heterocyclic oxidation base is present in an amount ranging from about 0.005 to about 6% by weight relative to the total weight of the dye composition.

13. A composition according to claim 1, wherein said at least one 3-aminopyridine derivative of formula (I) is chosen from:

4'-dimethylaminobenzene-1'-azo-1-methyl-3-pyridinium methosulphate of formula:

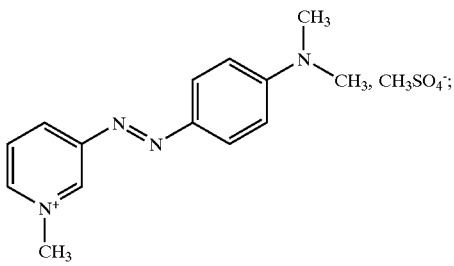

4'-bis(β-hydroxyethyl)aminobenzene-1'-azo-1-methyl-3-pyridinium methosulphate of formula:

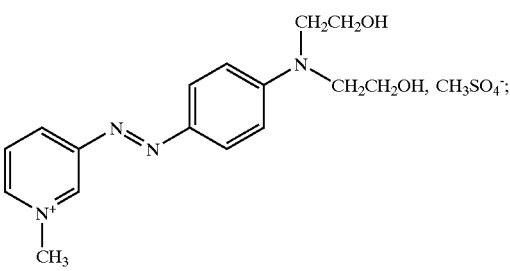

4'-amino-8'-hydroxynaphthalene-1'-azo-1-methyl-3-pyridinium methosulphate of formula:

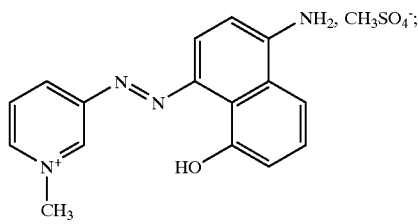

4'-dimethylamino-2'-nitrobenzene-1'-azo-1-methyl-3-pyridinium methosulphate of formula:

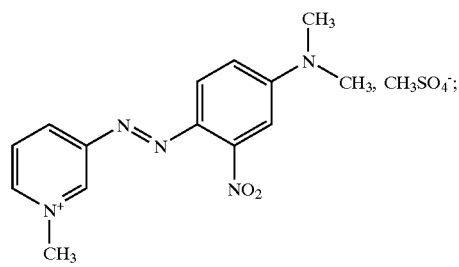

4'-dimethylaminobenzene-1'-azo-1,6-dimethyl-3-pyridinium methosulphate of formula:

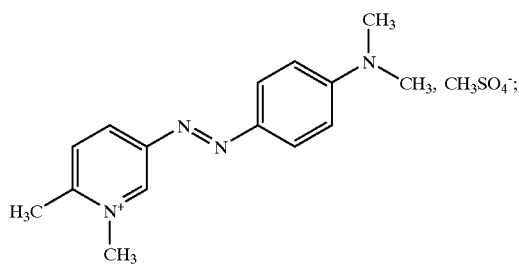

4'-aminobenzene-1'-azo-3-pyridine N-oxide of formula:

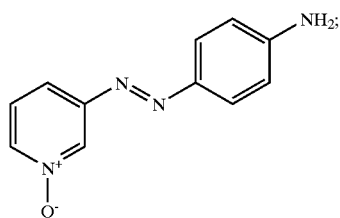

4'-dimethylaminobenzene-1'-azo-3-pyridine N-oxide of formula:

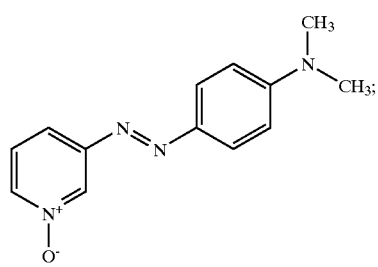

4'-N,N-bis(β-hydroxyethyl)aminobenzene-1'-azo-3-pyridine N-oxide of formula:

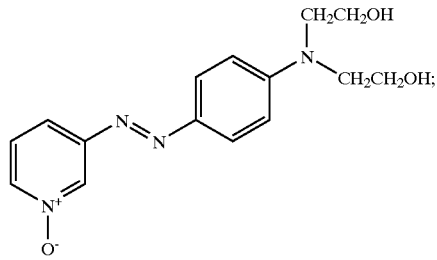

4'-dimethylamino-2'-methylbenzene-1'-azo-1-ethyl-3-pyridinium ethosulphate of formula:

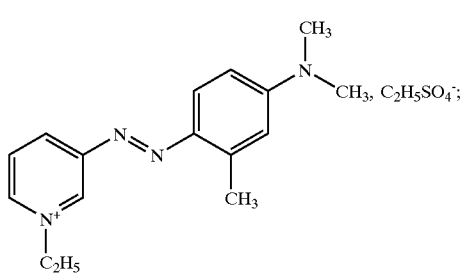

4'-dimethylamino-2'-methylbenzene-1'-azo-1-butyl-3-pyridinium bromide of formula:

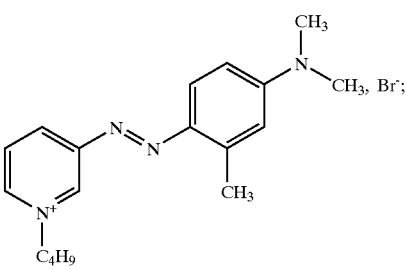

4'-dimethylamino-2'-chlorobenzene-1'-azo-1-methyl-3-pyridinium methosulphate of formula:

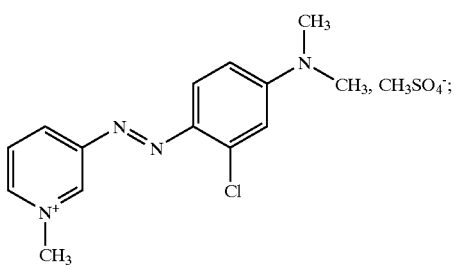

2',4'-diamino-5'-methylbenzene-1'-azo-1-methyl-3-pyridinium methosulphate of formula:

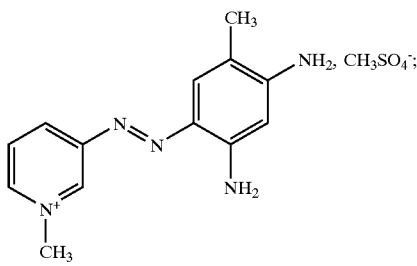

4'-phenylaminobenzene-1'-azo-1-methyl-3-pyridinium methosulphate of formula:

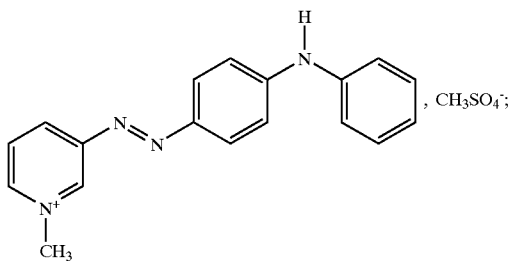

2'-acetylamino-4'-dimethylaminobenzene-1'-azo-1-ethyl-3-pyridinium ethosulphate of formula:

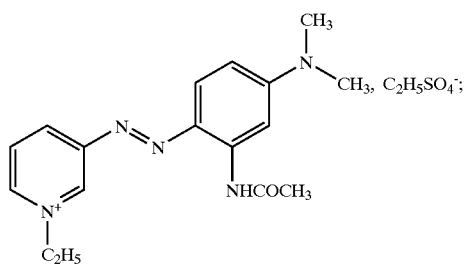

2',4'-diamino-5'-methoxybenzene-1'-azo-1-methyl-3-pyridinium methosulphate of formula:

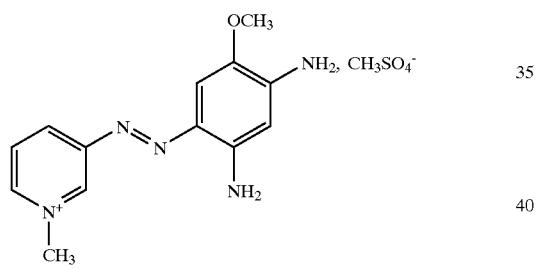

and

2'-amino-4'-dimethylaminobenzene-1'-azo-1-methyl-3-pyridinium methosulphate of formula:

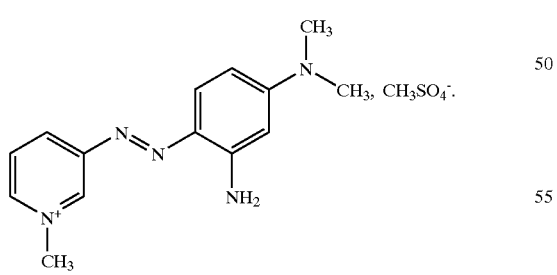

14. A composition according to claim 1, wherein said at least one 3-amino-pyridine derivate of formula (I) is present in an amount ranging from about 0.001 to about 10% by weight relative to the total weight of the dye composition.

15. A composition according to claim 14, wherein said at least one 3-aminopyridine derivative of formula (I) is present in an amount ranging from about 0.01 to about 5% by weight relative to the total weight of the dye composition.

16. A composition according to claim 1, further comprising at least one coupler, at least one benzenic oxidation base, at least one direct dye other than said at least one 3-aminopyridine derivative of formula (I), or mixtures thereof.

17. A composition according to claim 1, wherein said acid addition salts are chosen from hydrochlorides, hydrobromide sulphates, tartrates, lactates and acetates.

18. A composition according to claim 4, wherein said medium suitable for dyeing comprises water or a mixture of water and at least one organic solvent.

19. A composition according to claim 1, wherein said composition has a pH ranging from about 3 to about 12.

20. A process for dyeing keratin fibers comprising
a) applying to said keratin fibers an oxidation dyeing composition comprising at least one heterocyclic oxidation base chosen from pyridine derivatives and pyrimidine derivatives, and acid addition salts thereof, and, as a direct dye, at least one 3-aminopyridine derivative chosen from the compounds of formula (I):

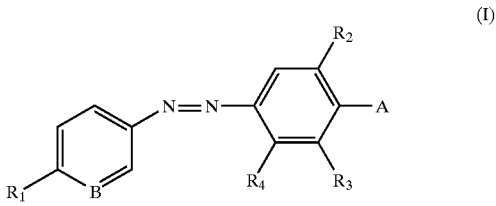

in which:
B is chosen from formula (Ia) or (Ib):

R is a $C_1$–$C_4$ alkyl radical;
$R_1$ is chosen from a hydrogen atom, a halogen atom, a $C_1$–$C_4$ alkyl radical, and a $C_1$–$C_4$ alkoxy radical;
$R_2$ is chosen from a hydrogen atom, a $C_1$–$C_4$ alkyl radical and a $C_1$–$C_4$ alkoxy radical;
$R_4$ is chosen from a hydrogen atom, a halogen atom, a $C_1$–$C_4$ alkyl radical, a nitro radical, an amino radical and a ($C_1$–$C_4$)acylamino radical;
$R_3$ is a hydrogen atom, or $R_4$ and $R_3$ together form a 6-membered unsaturated ring bearing a hydroxyl substituent chelated with one of the nitrogen atoms of the azo double bond;
A is a residue —$NR_5R_6$ in which $R_5$ is chosen from a hydrogen atom, a $C_1$–$C_4$ alkyl radical, a $C_1$–$C_4$ monohydroxyalkyl radical and a $C_2$–$C_4$ polyhydroxyalkyl radical; and $R_6$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a phenyl ring and a —$CH_2$—$SO_3Na$ radical; and
$X^-$ is chosen from a monovalent anion and a divalent anion; and b) developing a color at an acidic, neutral or alkaline pH with the aid of an oxidizing agent, wherein said oxidizing agent is added to said oxidation dyeing composition at the time of application of said oxidation dyeing composition, or wherein said oxidizing agent is present in an oxidizing composition, and wherein said oxidizing composition is applied simultaneously or sequentially with said oxidation dyeing composition.

21. A process according to claim 20, wherein said oxidizing agent present in said oxidizing composition is chosen from hydrogen peroxide, urea peroxide, alkali metal bromates, persalts, peracids and enzymes.

22. A process according to claim 21, wherein said persalts are chosen from perborates, percarbonates and persulfates.

23. A multi-compartment dyeing device or kit for dyeing keratin fibers, comprising at least two compartments, wherein one compartment comprises an oxidizing composition, and the other compartment comprises a composition for the oxidation dyeing of keratin fibers, said composition for the oxidation dyeing of keratin fibers comprising:
   a) at least one heterocyclic oxidation base chosen from pyridine derivatives and pyrimidine derivatives, and acid addition salts thereof, and
   b) as direct dye, at least one 3-aminopyridine derivative chosen from the compounds of formula (I):

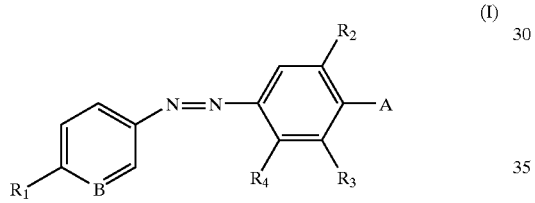

(I)

in which:
B is chosen from formula (Ia) or (Ib):

(Ia)

(Ib)

R is a $C_1$–$C_4$ alkyl radical;

$R_1$ is chosen from a hydrogen atom, a halogen atom, a $C_1$–$C_4$ alkyl radical, and a $C_1$–$C_4$ alkoxy radical;

$R_2$ is chosen from a hydrogen atom, a $C_1$–$C_4$ alkyl radical and a $C_1$–$C_4$ alkoxy radical;

$R_4$ is chosen from a hydrogen atom, a halogen atom, a $C_1$–$C_4$ alkyl radical, a nitro radical, an amino radical and a ($C_1$–$C_4$)acylamino radical;

$R_3$ is a hydrogen atom, or $R_4$ and $R_3$ together form a 6-membered unsaturated ring bearing a hydroxyl substituent chelated with one of the nitrogen atoms of the azo double bond;

A is a residue —$NR_5R_6$ in which $R_5$ is chosen from a hydrogen atom, a $C_1$–$C_4$ alkyl radical, a $C_1$–$C_4$ monohydroxyalkyl radical and a $C_2$–$C_4$ polyhydroxyalkyl radical; and $R_6$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a phenyl ring and a —$CH_2$—$SO_3Na$ radical; and $X^-$ is chosen from a monovalent anion and a divalent anion.

* * * * *

UNITED STATES PATENT AND TRADEMARK OFFICE
CERTIFICATE OF CORRECTION

PATENT NO.   : 6,797,013 B1
DATED         : September 28, 2004
INVENTOR(S)  : Gérard Lang et al.

It is certified that error appears in the above-identified patent and that said Letters Patent is hereby corrected as shown below:

<u>Column 12,</u>
Lines 23-24, "2,5 N7,N7-tetramethylpyrazolo[1,5-a] pyrimidine-3,7-diamine," should read -- 2,5, N7,N7-tetramethylpyrazolo[1,5-a]pyrimidine-3,7-diamine, --.

<u>Column 15,</u>
Line 61, "derivate" should read -- derivative --.

<u>Column 16,</u>
Lines 7-8, "hydrobromide sulphates," should read -- hydrobromides, sulphates, --.

Signed and Sealed this

Eleventh Day of January, 2005

JON W. DUDAS
*Director of the United States Patent and Trademark Office*